United States Patent [19]

Jansen et al.

[11] Patent Number: 5,047,293

[45] Date of Patent: Sep. 10, 1991

[54] FIXED DRESSINGS WITH GREATLY REDUCED FOAMING

[75] Inventors: Bernhard Jansen, Cologne; Hanns-Peter Müller, Bergisch-Gladbach; Roland Richter, Leverkusen, all of Fed. Rep. of Germany

[73] Assignee: Bayer Aktiengesellschaft, Leverkusen, Fed. Rep. of Germany

[21] Appl. No.: 522,294

[22] Filed: May 11, 1990

[30] Foreign Application Priority Data

Jun. 3, 1989 [DE] Fed. Rep. of Germany ....... 3918177

[51] Int. Cl.⁵ ................. B32B 17/04; C08G 9/00; A61F 5/04
[52] U.S. Cl. .................. 428/423.1; 428/447; 428/317.3; 428/290; 428/254; 428/266; 428/273; 521/110; 128/90; 128/82
[58] Field of Search ............... 128/90, 82; 428/447, 428/262, 423.3, 695, 900, 221, 254, 423.1, 317.3, 900; 521/110, 112; 528/12, 59

[56] References Cited

U.S. PATENT DOCUMENTS 4,031,044  6/1977  Joslyn ..................... 521/112
4,347,330  8/1982  Demou et al. .................. 521/110
4,574,793  3/1986  Lee et al. ................... 128/90
4,643,909  2/1987  Kammerer .................... 128/90
4,855,379  8/1989  Budnik et al. ................. 521/110

*Primary Examiner*—George F. Lesmes
*Assistant Examiner*—Richard Weisberger
*Attorney, Agent, or Firm*—Sprung Horn Kramer & Woods

[57] ABSTRACT

Foaming during setting of a polyurethane fixed dressing, e.g. cast for broken arm, is minimized by utilizing as the dressing a polyisocyanate composition comprising:
  a) at least one organic polyisocyanate,
  b) at least one catalyst and
  c) at least one compound of the formula

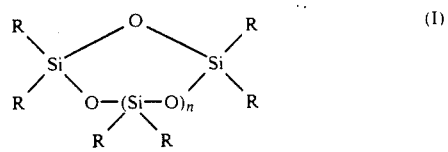

in which R represents methyl, ethyl or propyl and $1 \leq n \leq 4$.

6 Claims, No Drawings

FIXED DRESSINGS WITH GREATLY REDUCED FOAMING

The invention relates to fixed dressings which contain a novel polyisocyanate preparation on a backing material, a process for the preparation thereof and the use of the polyisocyanate preparations on a backing material for fixed dressings.

The use of dressings impregnated with gypsum as the reinforcing dressing material is known. Casts of this type are inconveniently heavy, have low air permeability, and rapidly lose strength in the moist state, for example owing to the effect of water on the hardened dressing; they prevent the diagnostic evaluation of X-ray photographs owing to their X-ray absorption and scattering and, owing to their poor water resistance, they often bring about skin irritations caused by bacterial or mold growth in the dressing.

DE-C-2,357,931 describes fixed dressings whose curing principle is the reaction between isocyanate groups and water molecules. The dressing materials are composed of a flexible backing material which is impregnated and/or coated with a compound having isocyanate groups, preferably an isocyanate prepolymer. However, in this instance no substances are used which are intended to prevent foaming.

DE-C-2,651,089 proposes the use, as curable component of the fixed dressing, of a prepolymer having aromatic isocyanate groups which contains a certain amount of nitrogen. According to EP-B-86, 621, the curing reaction of the isocyanate prepolymer is accelerated using bismorpholinodiethyl ether, a catalyst which has little adverse effect on the shelf life of the prepolymer.

Both applications mention polydimethylsiloxanes, in one instance of low viscosity and in the other instance of high viscosity, as surface—active substances for preventing vigorous foaming.

All polyisocyanate preparations for fixed dressings have in common that they generate foam, which is hardly surprising owing to the carbon dioxide formed in the isocyanate-water reaction.

However, this foaming is most inconvenient. Some of the reasons why:

Excessive foaming causes poor interlayer bonding in the cured dressing owing to gas bubbles;

Foaming results in the amount of polyisocyanate preparation per unit mass of backing material having to be reduced and does not allow high strength to be achieved in the cured dressing.

Even slight foaming seals off the channels provided in the fabric in the cured dressing and so eliminates the air permeability which is one of the greatest advantages of polyisocyanate fixed dressings.

It is clear that the key to an improved polyurethane fixed dressing is the prevention of foaming.

The object of the present invention is therefore to eliminate the abovementioned disadvantages. However, the prior art polydimethylsiloxanes are often poorly miscible with the polyisocyanate preparations owing to their highly hydrophobic character, particularly if the polyisocyanates are of relatively high molecular weight.

The present invention accordingly provides fixed dressings which contain a polyisocyanate preparation on a flexible backing material, the polyisocyanate preparation being composed of:

a) at least one organic polyisocyanate,
b) at least one catalyst and
c) auxiliaries and additives, characterized in that the auxiliaries and additives used are compounds of the structure I

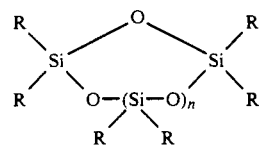

in which R = methyl, ethyl or propyl and $1 \leq n \leq 4$, preference however being given to the compound

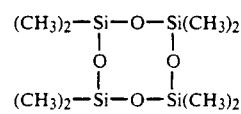

known as octamethyl-cyclotetrasiloxane.

A feature of the fixed dressings according to the invention is that the cured dressings do not give rise to any foaming at all even when the amount of polyisocyanate preparation is 70–90% of the weight of the backing material.

In addition, the use of the polyisocyanate preparations according to the invention allows a higher degree of resinification of the backing material. This is also of great importance for industrial applications, since an optically flowless surface of the article, together with high strength, is obtained without the use of any further auxiliaries.

Particularly surprising for those skilled in the art is the fact that the compounds of the structure I, despite their low molecular weight cyclic character, have a better antifoam action than the higher molecular weight polydimethylsiloxanes from the category of the surface—active substances. Indeed, the low molecular weight character of the substance is a great advantage since mixing with an isocyanate preparation is made significantly easier and furthermore there is no danger of phase separation.

The component a) of the polyisocyanate preparation according to the invention is composed of at least one organic polyisocyanate, i.e. of any compounds or mixtures of compounds which have at least two organically bound isocyanate groups per molecule.

This includes not only low molecular weight polyisocyanates having a molecular weight below 400 but also modifications of this type of low molecular weight polyisocyanate having a molecular weight, calculable from the functionality and the proportion of functional groups, of between 400 and 10,000, preferably between 600 and 8,000 and in particular from 800 to 5,000. Examples of suitable low molecular weight polyisocyanates are those of the formula $$Q(NCO)_n, \qquad (II)$$

in which
$n = 2$ to 4, preferably 2,
and
Q denotes an aliphatic hydrocarbon radical having 2 to 18, preferably 6 to 10 carbon atoms, a cycloaliphatic hydrocarbon radical having 4 to 15, preferably 5 to 10 carbon atoms, an aromatic hydrocarbon radical having 6 to 15, preferably 6 to 13 carbon atoms, or an araliphatic hydrocarbon radical having 8 to 15, preferably 8 to 13 carbon atoms.

Examples of suitable low molecular weight polyisocyanates of this type are hexamethylene diisocyanate, 1,12-dodecane diisocyanate, 1,3-cyclobutane diisocyanate, 1,3-cyclohexane diisocyanate and 1,4-cyclohexane diisocyanate and also any mixtures of these isomers, 1-isocyanato-3,3,5-trimethyl-5 -isocyanatomethylcyclohexane, 1,3-hexahydrophenylene diisocyanate and/or 1,4-hexahydrophenylene diisocyanate, 2,4'-perhydrodiphenylmethane diisocyanate and/or 4,4'-perhydrodiphenylmethane diisocyanate, 1,3-phenylene diisocyanate and 1,4-phenylene diisocyanate, 2,4-toluene diisocyanate and 2,6-toluene diisocyanate and also any mixtures of these isomers, 2,4'-diphenylmethane diisocyanate and/or 4,4'-diphenylmethane diisocyanate, 1,5-naphthylene diisocyanate, 4,4',4''-triphenylmethane triisocyanate or polyphenyl-polymethylene polyisocyanates, as obtained by aniline-formaldehyde condensation and subsequent reaction with phosgene. Suitable higher molecular weight polyisocyanates are modifications of simple polyisocyanates of this type, i.e. polyisocyanates having, for example, isocyanurate, carbodiimide, allophanate, biuret or uretdione structural units, such as can be prepared by prior art processes known per se from the simple polyisocyanates of the above-mentioned formula which were given as examples above. The higher molecular weight, modified polyisocyanates of particular interest are those prepolymers known from polyurethane chemistry having terminal isocyanate groups and molecular weights in the range from 400 to 10,000, preferably 600 to 8,000 and particularly 800 to 5,000. These compounds are prepared in a manner known per se by reacting excess amounts of simple polyisocyanates of the type mentioned above by way of example with organic compounds having at least two groups which are reactive towards isocyanate groups, in particular organic polyhydroxy compounds. Suitable polyhydroxy compounds of this type are not only simple polyhydric alcohols in the molecular weight range of 62 to 599, preferably 62 to 200, such as for example ethylene glycol, trimethylolpropane, 1,2-propanediol or 1,2-butanediol, but also in particular higher molecular weight polyetherpolyols and/or polyesterpolyols of the type known per se from polyurethane chemistry having molecular weights from 600 to 8,000, preferably 800 to 4,000, and at least two, as a rule 2 to 8, preferably however 2 to 4 primary and/or secondary hydroxyl groups. Obviously, it is also possible to use those NCO-prepolymers which have been obtained for example from low molecular weight polyisocyanates of the type mentioned above by way of example and less preferred compounds having groups which are reactive towards isocyanate groups, such as for example polythioetherpolyols, hydroxyl-containing polyacetals, polyhydroxypolycarbonates, hydroxyl-containing polyesteramides or hydroxyl-containing copolymers of olefinically unsaturated compounds. Suitable compounds for the preparation of the NCO-prepolymers, the said compounds having groups, in particular hydroxyl groups, which are reactive towards isocyanate groups, are for example the compounds disclosed in US-A-4,218,543, column 7, line 29 to column 9, line 25 as examples. The NCO-prepolymers are prepared by reacting these compounds having groups which are reactive towards isocyanate groups with simple polyisocyanates of the type mentioned above by way of example while observing a ratio of equivalents of NCO/OH of about 1.5:1 to 20:1, preferably 5:1 to 15:1. Generally, the NCO-prepolymers have an NCO content of 2.5 to 25, preferably 6 to 22% by weight. It follows already from this that within the scope of the present invention the terms "NCO-prepolymers" and "prepolymers having terminal isocyanate groups" are understood to include not only the reaction products as such but also mixtures of the reaction products with excess amounts of unconverted polyisocyanate starting materials, these mixtures often being referred to also as "semiprepolymers".

In the process according to the invention, particular preference is given to polyisocyanate components a) which are industrial polyisocyanates customary in polyurethane chemistry, i.e. hexamethylene diisocyanate, 1-isocyanato-3,3,5-trimethyl-5-isocyanatomethyl-cyclohexane (isophorone diisocyanate, abbreviated as IPDI), 4,4'-diisocyanatodicyclohexylmethane, 2,4-diisocyanatotoluene, its industrial mixtures with 2,6-diisocyanatotoluene, 4,4'-diisocyanatodiphenylmethane, its mixtures with the corresponding 2,4'- and 2,2'-isomers, polyisocyanate mixtures of the diphenylmethane series such as are obtained in a manner known per se by reacting aniline/formaldehyde condensates with phosgene, the modifications of these industrial polyisocyanates containing biuret groups or isocyanurate groups, and in particular NCO-prepolymers of the type mentioned above based on these industrial polyisocyanates on the one hand and on the simple polyols mentioned above by way of example and/or polyetherpolyols and/or polyesterpolyols on the other hand, and also to any mixtures of polydiisocyanates of this type.

The catalyst component b) is an amine catalyst, preferably however a bismorpholinodiethyl ether as used in EP-B-86,621 or a tin catalyst, preferably however dialkyltin dilaurate blocked with tosyl isocyanate as described in DE-C-3,326,566.

Preference is also given to the likewise catalytically effective polyethers which have been polymerized initially in the presence of amines and by virtue of a tertiary amine content of 0.05 to 10% by weight, preferably however 0.1 to 1% by weight (based on the total isocyanate preparation) determine the curing times of the prepolymers described under a) and enter the formulation as a component of the prepolymers mentioned on page 7.

The auxiliaries and additives c) include octamethylcyclotetrasiloxane; the amount used is: 0.01 to 7% by weight, preferably 0.02 to 5% by weight, particularly preferably 0.05 to 4% by weight.

Other components c) may optionally include solvents known from adhesives technology and paint technology such as for example toluene, xylene, ethyl acetate, butyl acetate, methyl ethyl ketone, methyl isobutyl ketone, ethylene glycol monoethyl ether acetate or any mixtures of such solvents. Examples of other components c) are pigments, fillers or flow—control agents and also UV stabilizers.

Suitable backing materials are solid or porous films and also foams made from natural or synthetic materials (for example polyurethane) but primarily airpermeable, flexible sheet-like structures based on textiles, preferably having a weight of 20 to 1,000 g/m², in particular 30 to 500 g/m². Examples of sheet-like structures are the following:

1. Woven or knitted textile fabrics with a basis weight of 20 to 200 g/m², preferably 40 to 100 g/m², and with a thread count preferably of 2 to 20 threads per linear centimeter in the longitudinal and transverse directions. The woven or knitted textile fabric can be prepared from any natural or synthetic yarns. However, preference is given to the use of woven or knitted fabrics which have been obtained from cotton yarns or from mixed yarns which for their part have been obtained not only from hydrophobic yarns or fibers having a high modulus of elasticity (for example polyesters) but also hydrophilic natural or synthetic yarns or fibers (for example cotton or polyamide).
2. Preference is given to woven or knitted glass fiber fabrics with a weight of 60 to 500 g/m², preferably 100 to 400 g/m², prepared from glass fiber yarns with a modulus of elasticity of 7,000 to 9,000 (daN/mm²) and a thread count of 3 to 10, preferably 5 to 7 in the longitudinal direction and with a thread count of 3 to 10, preferably 4 to 6 in the transverse direction per centimeter of glass fiber fabric, and which have, by virtue of a particular type of heat treatment, a longitudinal elasticity of 10 to 30%. The knitted fabric may be either sized or unsized.
3. Non-bonded or bonded or needled webs based on inorganic and preferably organic fiber and having a weight of 30 to 400 g/m², preferably 50 to 200 g/m².

The preparation of reinforcing dressings according to the invention in the form of shells or splints is also possible with the aid of webs having weights of up to 1,000 g/m². Examples of suitable backing materials according to the invention are also described in US-A-4,134,397, US-A-3,686,725, US-A-3,882,857, DE-C-3,211,634 and EP-B-61,642.

In the fixed dressings according to the invention, the backing material is coated and/or impregnated with an amount of 25 to 90% by weight, preferably 25 to 80% by weight, particularly preferably 30 to 75% by weight, based on the total fixed dressing.

The present invention also provides a process for the preparation of fixed dressings which is characterized in that, with the exclusion of moisture, a polyisocyanate preparation is used comprising
  a) at least one organic polyisocyanate,
  b) at least one catalyst and
  c) auxiliaries and additives, the auxiliary and additive according to the invention being a compound of the structure I, preferably however being octamethyl-cyclotetrasiloxane.

The process according to the invention is carried out with the exclusion of moisture, preferably at a relative humidity of less than 1% (at 21° C.), particularly preferably at less than 0.5% (at 21° C.).

Coating or impregnation can be carried out with the polyisocyanate preparation dissolved in an inert solvent which can be evaporated off again after the coating operation.

Examples of inert solvents are chlorinated hydrocarbons such as methylene chloride, trichloroethane or chloroform, ketones such as acetone and methyl ethyl ketone, esters such as ethyl acetate and butyl acetate, aromatics such as toluene or xylene, or suitable derivatives which contain no Zerewitinoff-active hydrogen.

The fixed dressings according to the invention can for example be prepared as follows:

Generally the backing material is passed over a roller and impregnated with the polyisocyanate preparation which may optionally be in a solvent. Immediately after coating or impregnation, the dressing material is rolled up on suitable spools in the required length (as a rule 2 to 11 meters) and is sealed up in an air- and water-tight film (for example made from plastic-aluminum laminate) or in other fully sealed containers, as described in DE-A-2,357,931, DE-A-2,651,089 and DE-A-3,033,569.

Immediately before use, the material is removed from the packaging and wound around the part of the body which is to be protected and which has optionally first been wound with a suitable cushioning or lining material (for example polyester web).

For curing with water, catalyst concentrations for example of 0.01 to 15% by weight, particularly preferably of 0.5 to 12% by weight, are used.

For curing with moisture, catalyst concentrations of 1.0 to 15% by weight, preferably 2.0 to 14% by weight, are used.

The curing reaction of the dressing material according to the invention preferably does not begin immediately on contact with water. The actual crosslinking reaction between isocyanate groups and water only commences after a certain time, which can be adjusted again for its part via the catalyst concentration. During this initial phase of curing, the dressing can be applied and shaped.

Example 1

Preparation of a water-curing reactive resin according to the invention (using the additive according to the invention)

A 10 l sulphuration vessel with a stainless steel anchor-stirrer is first charged with 64.0 parts of isocyanate [bis(4-isocyanatophenyl)methane] which contains carbodiimidized components [NCO content=29%]. Then 0.08 parts of the auxiliary and additive octamethylcyclotetrasiloxane and 0.04 parts of benzoyl chloride are added followed by 19.7 parts of a polyether prepared by propoxylation of propylene glycol (OH number=112 mg of KOH/g), 13.24 parts of a polyether prepared by propoxylation of propylene glycol (OH number=250 mg of KOH/g) and 1.7 parts of dimorpholinodiethyl ether.

At the end, the isocyanate content is 13.2%, and the viscosity is 25,500 mPa.s (23° C.).

Example 2

Preparation of a water-curing reactive resin according to the invention [using a prior art additive (comparative example)]

A 10 l sulphuration vessel with a stainless steel anchor-stirrer is first charged with 64.0 parts of isocyanate [bis(4-isocyanatophenyl)methane] which contains carbodiimidized components (NCO content=29%). Then 0.08 parts of a polydimethylsiloxane with $\gamma=30,000$ mPa.s and 0.04 parts of benzoyl chloride are added followed by 19.7 parts of a polyether prepared by propoxylation of propylene glycol (OH number=112 mg of KOH/g), 13.24 parts of a polyether prepared by propoxylation of propylene glycol (OH number=250 mg of KOH/g) and 1.7 parts of dimorpholinodiethyl ether.

At the end, the isocyanate content is 13.2% and the viscosity is 25,500 mPa.s (23° C.).

Example 3

Preparation of a water-curing reactive resin (example using an additive according to the invention)

A 10 l sulphuration vessel with a stainless steel anchor-stirrer is first charged with 66 parts of isocyanate (bis(4-isocyanatophenyl)methane) which contains carbodiimidized components [NCO content=29%] and the mixture is preheated to about 50° C. To this are added 1.5 parts of a UV stabilizer (a cyanoalkylindole derivative) and stirring is continued until all of the solid has dissolved. After cooling to room temperature, 34 parts of propoxylated triethanolamine (OH number=150 mg of KOH/g) are added over a period of 10 minutes. After briefly rising to 55° C. after 55 minutes, the temperature falls again, whereupon 0.5 parts of the auxiliary and additive octamethylcyclotetrasiloxane are added and after 2 hours the isocyanate content reaches 13.4%. The isocyanate content of the finished prepolymer is 12.7%, and the viscosity is 14,640 m.Pas (25° C.).

Example 4

Preparation of a water-curing reactive resin (comparative example using a prior art additive)

A 10 l sulphuration vessel with a stainless steel anchor-stirrer is first charged with 66 parts of isocyanate (bis(4-isocyanatophenyl)methane) which contains carbodiimidized components [NCO content =29%] and the mixture is preheated to about 50° C. To this are added 1.5 parts of a UV stabilizer (a cyanoalkylindole derivative) and stirring is continued until all of the solid has dissolved. After cooling to room temperature, 34 parts of propoxylated triethanolamine (OH number=150 mg of KOH/g) are added over a period of 10 minutes. After briefly rising to 55° C. after 55 minutes, the temperature falls again, whereupon 0.5 parts of a polydimethylsiloxane with $\gamma=200$ mPa.s are added and after 2 hours the isocyanate content reaches 13.4%. The isocyanate content of the finished prepolymer is 12.7%, and the viscosity is 14,640 mPa.s (25° C.).

Example 5

Preparation of test dressings with the reactive resins from Examples 1-4

Example 5a

A glass fiber knitted fabric (width 10.0 cm, basis weight about 290 g/m²) which has an elongation of about 65% in the longitudinal direction (a detailed description of this knitted fabric is to be found in US-A-4,609,578) is coated according to Example 3 with 70% by weight (on weight of fiber) of the resin. The coating operation is carried out in an atmosphere whose relative humidity corresponds to a water dew point of below −20° C. The resin is applied homogeneously to the knitted fabric using a suitable roller-impregnation means. A suitable apparatus is described in detail in US-A-4,427,002. After coating, 3.66 m of this tape are wound up on a plastic spool 1 cm in diameter and sealed up in a water vapor-impermeable film.

Example 5b

Similarly to Example (5a), the glass fiber knitted fabric is coated with 70% by weight (on weight of fiber) of the resin from Example 4 and packaged.

Example 5c

Similarly to Example (5a), a polyester knitted fabric (width 10.0 cm, basis weight 118 g/m²) which has an elongation in the longitudinal direction of about 55% and an elongation in the transverse direction of about 90% and which has, in the wales, a 167-dtex 30-filament textured polyester yarn and, in the course, a 550 dtex 96—filament normal-shrinkage high—tenacity polyester yarn is coated with 136% by weight (on weight of fiber) of the resin from Example 1 and packaged.

Example 5d

Similarly to Example (5a), the polyester knitted fabric described in Example (5c) is coated with 136% by weight (on weight of fiber) of the resin from Example 2 and packaged.

Example 5e

Similarly to Example (5a), the polyester knitted fabric described in Example (5c) is coated with 155% by weight (on weight of fiber) of the resin from Example 1 and packaged.

Example 5f

Similarly to Example (5a), the polyester knitted fabric described in Example (5c) is coated with 155% by weight (on weight of fiber) of the resin from Example 2 and packaged.

Example 6

Curing of the test dressings described in Example 5 and determination of the air permeability of the resulting wound structures.

Immersion in water is used to wet the fixed dressings from Examples 5a to 5f and these dressings are wound on a cylinder with an external diameter of 7.5 cm so that wound structures with an internal diameter of 7.5 cm are obtained.

After curing and complete drying of the test structure, the air permeability of the latter can be determined from the flow resistance to air being blown through it. The values obtained with the test dressings from Examples 5a to 5f are summarized in the following table.

TABLE

| Test dressing according to Example | Additive according to the invention | Measured air permeability in % |
|---|---|---|
| 5a | Yes | 82 |
| 5b | No | 17 |
| 5c | Yes | 85 |
| 5d | No | 60 |
| 5e | Yes | 40 |
| 5f | No | 15 |

It is noteworthy that the novel auxiliary and additive octamethylcyclotetrasiloxane has no adverse effect on the shelf life of the isocyanate reactive resins.

It is understood that the specification and examples are illustrative but not limitative of the present invention and that other embodiments within the spirit and scope of the invention will suggest themselves to those skilled in the art.

We claim:

1. A fixed dressing comprising a polyisocyanate composition on a flexible backing material, the polyisocyanate composition consisting essentially of:
   a) at least one organic polyisocyanate, b) at least one catalyst and c) at least one compound of the formula

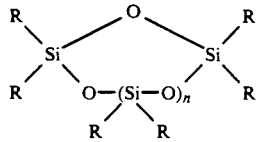

in which R represents methyl, ethyl or propyl and $1 \leq n \leq 4$.

2. A fixed dressings according to claim 1, wherein (c) comprises the compound octamethylcyciotetrasiloxane of the formula

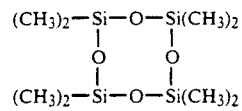

3. A fixed dressing according to claim 1, wherein (c) is present in about 0.01 to 7% by weight.

4. A fixed dressing according to claim 1, wherein (a) is a polyisocyanate having a molecular weight below 400, a derivative of this type of low molecular weight polyisocyanate having a molecular weight, calculable from the functionality and the proportion of functional groups, of between 400 and 10,000 or a higher molecular weight polyisocyanate having isocyanurate, carbodiimide, allophanate, biuret or uretdione structural units.

5. A fixed dressing according to claim 1, wherein the catalyst(b) is an anionic catalyst or a polyether which has been polymerized initially in the presence of an amine.

6. A fixed dressing according to claim 1, wherein the backing material is a solid or porous film or foam made from a natural or synthetic material or an air permeable, flexible textile structure.

* * * * *

UNITED STATES PATENT AND TRADEMARK OFFICE
CERTIFICATE OF CORRECTION

PATENT NO. : 5,047,293

DATED : September 10, 1991

INVENTOR(S) : Jansen et al.

It is certified that error appears in the above-identified patent and that said Letters Patent is hereby corrected as shown below:

Col. 9, line 24, delete "octamethylcyciotetrasiloxane" and substitute --octamethylcyclotetrasiloxane--

Signed and Sealed this

Twenty-first Day of September, 1993

Attest:

BRUCE LEHMAN

Attesting Officer

Commissioner of Patents and Trademarks